United States Patent [19]

Kampe et al.

[11] 3,966,916

[45] June 29, 1976

[54] N(6)-DISUBSTITUTED ADENOSINE COMPOUNDS AND THERAPEUTIC COMPOSITIONS

[75] Inventors: Wolfgang Kampe, Heddesheim; Erich Fauland; Kurt Stach, both of Mannheim-Waldhof; Harald Stork, Mannheim-Feudenheim; Felix Helmut Schmidt, Mannheim-Seckenheim, all of Germany

[73] Assignee: Boehringer Mannheim G.m.b.H., Mannheim-Waldhof, Germany

[22] Filed: Nov. 21, 1974

[21] Appl. No.: 525,795

Related U.S. Application Data

[62] Division of Ser. No. 393,859, Sept. 4, 1973, Pat. No. 3,880,829.

[30] Foreign Application Priority Data

Sept. 9, 1972 Germany............................ 2244328

[52] U.S. Cl............................ 424/180; 260/211.5 R
[51] Int. Cl.². ................................................ A61K 31/70
[58] Field of Search................... 424/180; 260/211.5

[56] References Cited
UNITED STATES PATENTS
3,551,409   12/1970   Kampe et al........................ 424/180

Primary Examiner—Johnnie R. Brown
Attorney, Agent, or Firm—Burgess, Dinklage & Sprung

[57] ABSTRACT

New N(6)-disubstituted adenosine compound of the formula

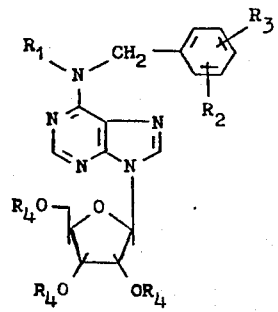

wherein
$R_1$ is lower alkyl substituted by at least one of hydroxyl, alkoxy or acyloxy; or is cycloalkyl or straight-chained or branched lower alkenyl;
$R_2$ and $R_3$ are hydrogen, halogen, or nitro or lower alkyl, alkoxy or alkylthio and
$R_4$ is hydrogen or acyl; when $R_4$ is acyl, $R_1$ can also be lower alkyl;
and the pharmacologicaly compatible salts thereof; exhibits shown anti-lipolytic, anti-hyperlipaemic and anti-hypercholesterolaemic action.

29 Claims, No Drawings

N(6)-DISUBSTITUTED ADENOSINE COMPOUNDS AND THERAPEUTIC COMPOSITIONS

This is a division of application Ser. No. 393,859 filed Sept. 4, 1973, now U.S. Pat. No. 3,880,829.

The present invention relates to new N(6)-disubstituted adenosine compounds and with therapeutic compositions containing them.

The new N(6)-disubstituted adenosine derivatives according to the present invention are compounds of the formula:

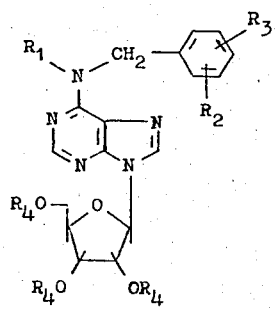

(I)

wherein $R_1$ is lower alkyl substituted by at least one of hydroxyl, alkoxy or acyloxy (i.e., alkanoyloxy); or is cycloalkyl or straight-chained or branched lower alkenyl;

$R_2$ and $R_3$, which may be the same or different, are hydrogen, halogen, or nitro or lower alkyl, alkoxy or alkylthio and $R_4$ is hydrogen or acyl (i.e., alkanoyl); when $R_4$ is acyl, $R_1$ can also be lower alkyl;

and the pharmacologically compatible salts thereof.

The alkyl, alkenyl, alkoxy and alkylthio radicals can contain up to 8 carbon atoms and preferably contain up to 4 carbon atoms. The cycloalkyl radicals can contain 3 to 9 ring carbon atoms and preferably contain 5 to 7 carbon atoms. The preferred acyl radicals include the formyl, acetyl, propionyl, butyryl and benzoyl radicals.

Surprisingly, it has been found that the new compounds of formula (I) possess only to a slight extent the cardiac and circulatory action usual for adenosine derivatives but that they have a strong anti-lipolytic, anti-hyperlipaemic and anti-hypercholesterolaemic action.

The new compounds of general formula (I) according to the present invention can be prepared, for example, by one of the following methods:

a. reaction of purine-ribosides of the general formula:

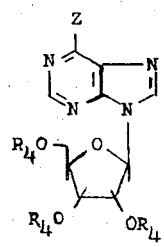

(II)

wherein $R_4$ has the same meaning as above and Z is a reactive residue, with amines of the general formula:

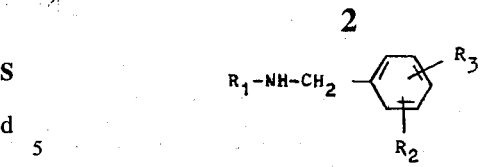

wherein $R_1$, $R_2$ and $R_3$ have the same meanings as above; optionally with intermediate protection of the hydroxyl groups of the sugar residue; or b. reaction of N(6)-substituted adenosine derivatives of the general formula:

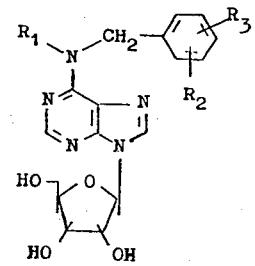

(IV)

wherein $R_1$, $R_2$ and $R_3$ have the same meanings as above, with acids of the general formula:

$R_5$ — OH     (V), wherein $R_5$ is an acyl radical, or with a reactive derivative thereof; whereafter, if desired; the compound obtained is converted into a pharmacologically compatible salt.

As reactive radical Z in the compounds of general formula (II), there can be used, for example, halogen atoms, reactive mercapto groups (especially methylthio and benzylthio groups) and the trimethylsilyloxy group.

For carrying out the process a) according to the present invention, the purine ribosides (II) are reacted with the amines (III) in an inert solvent, for example n-propanol, isopropanol, butanol, tetrahydrofuran or dioxan, preferably in the presence of a tertiary amine, for example triethylamine, at ambient temperature or at a slightly elevated temperature. If, during the reaction, acyl radicals are partially split off, then these can subsequently be replaced by means of process b).

As reactive derivatives of the acids (V), there can be used, for example, halides, anhydrides, azides, imidazolides or activated esters. The reaction with the compounds (IV) takes place, for example, under the conditions of the Schotten-Baumann reaction or with the addition of a tertiary amine, for example pyridine or dimethylaniline, in an inert solvent; an excess of the tertiary amine is preferably used.

If it is desired temporarily to block the hydroxyl groups of the compounds (II), then there can be used the protective groups which are conventional in sugar chemistry. For this purpose, there can be used acyl radicals, preferably acetyl or benzoyl radicals, or ketals can be used, for example the 2',3'-isopropylidene compounds, which can easily be split off again with acids after the condensation reaction, for example with the use of formic acid or of a dilute mineral acid, to give the free 2',3'-dihydroxy compound. When acyl radicals are used as protective groups, these can be split off by alkaline hydrolysis.

The pharmacologically compatible salts of the new compounds (I) can be obtained in the usual manner by neutralization of the free bases with non-toxic inorganic or organic acids, for example with hydrochloric acid, sulfuric acid, phosphoric acid, hydrobromic acid, acetic acid, lactic acid, citric acid, oxalic acid, malic acid, salicylic acid, malonic acid or succinic acid.

The purine ribosides (II) used as starting materials in which Z is a halogen atom are described in Coll, Czech. Chem. Comm., 30, 1880/1965; compounds (II) in which Z is a mercapto group are known from Chem. Pharm. Bull., 12, 951/1964; and compounds (II) in which Z is a trimethylsilyloxy radical are described in Ang. Chem., 84, 347/1972.

The following Examples are given for the purpose of illustrating the preparation of compounds of the present invention:

EXAMPLE 1

Preparation of N(6)-Cyclopentyl-N(6)-benzyladenosine 2.9 g. 6-Chloro-9-($\beta$-D-ribofuranosyl)-purine, 4.2 g. N-cyclopentylbenzylamine hydrochloride and 5.6 ml. triethylamine were heated under reflux in 50 ml. butanol for 10 hours. Thereafter, the solution was evaporated in a vacuum and the residue taken up in ethyl acetate. The ethyl acetate phase was washed with water, dried, clarified with active charcoal and evaporated. The residue solidified upon adding a little ethyl acetate and ether. After dissolving in ethyl acetate and reprecipitating with ether, there was obtained 1.0 g. (23% of theory) N(6)-cyclopentyl-N(6)-benzyl-adenosine, which sintered at 117°C.

EXAMPLE 2

Preparation of N(6)-Cyclohexyl-N(6)-(2-methylbenzyl)-adenosine 2.9 g. 6-Chloro-9-($\beta$-D-ribofuranosyl)-purine and 5.0 g. N-cyclohexyl-2-methylbenzylamine were heated under reflux for about 24 hours in 50 ml. butanol. Subsequently, the reaction mixture was evaporated in a vacuum and the residue taken up with ethyl acetate. The ethyl acetate phase was washed with dilute acetic acid and water, dried over anhydrous sodium sulfate and evaporated. The residue was first recrystallized from ether/heptane and then from acetonitrile. There were obtained 2.9 g. (64% of theory) N(6)-cyclohexyl-N(6)-(2-methylbenzyl)-adenosine, which had a melting point of 129°–130°C.

EXAMPLE 3

Preparation of N(6)-Cyclopentyl-N(6)-(2,5-dimethylbenzyl)-adenosine 21 g. Triacetyl-6-chloro-9-($\beta$-D-ribofuranosyl)-purine and 25 g. N-cyclopentyl-2,5-dimethylbenzylamine were boiled for 8 hours in 200 ml. butanol. After cooling the solution, it was mixed with ethereal hydrochloric acid until acidic, subsequently evaporated and the residue taken up in ethyl acetate/ether. N-cyclopentyl-2,5-dimethylbenzylamine hydrochloride which crystallized out was filtered off with suction and the filtrate was treated with active charcoal. The solution was then filtered and evaporated in a vacuum and the residue dissolved in 150 ml. methanol and mixed with 25 ml. 1N sodium methylate solution. The solution was boiled for 5–10 minutes, neutralized with acetic acid and evaporated. The residue was dissolved in ethyl acetate/ether and the organic phase was washed several times with water, again treated with active charcoal, dried and evaporated. The syrupy residue obtained crystallized from ether. There were obtained 14.3 g. (63% of theory) N(6)-cyclopentyl-N(6)-(2,5-dimethylbenzyl)-adenosine, which melted at 165°–167°C. By recrystallization from a little methanol, the melting point increased to 168°–170° C.

The following compounds were obtained in an analogous manner:
from triacetyl-6-chloro-9-($\beta$-D-ribofuranosyl)-purine and N-cyclopentyl-2,4-dimethylbenzylamine, there was obtained N(6)-cyclopentyl-N(6)2,4-dimethylbenzyl)-adenosine, which melted at 170°C; yield 20% of theory;
from triacetyl-6-chloro-9-($\beta$-D-ribofuranosyl)-purine and N-cyclopentyl-3,4-dimethylbenzylamine, there was obtained N(6)-cyclopentyl-N(6)-(3,4-dimethylbenzyl)-adenosine, which melted at 160°–161°C.; yield 45% of theory.

EXAMPLE 4

Preparation of N(6)-But-2-enyl-N(6)-(2,5-dimethylbenzyl)-adenosine 10 g. Triacetyl-6-chloro-9-($\beta$-D-ribofuranosyl)-purine, 5.7 g. N-but-2-enyl-(2,5-dimethylbenzyl)-amine and 2.5 g. triethylamine were heated under reflux for 1 hour in 150 ml. isopropanol. Subsequently, the solvent was removed in a vacuum and the residue taken up in chloroform. The chloroform phase was washed several times with water, dried and evaporated. The syrupy residue was dissolved in 150 ml. methanol and the solution mixed with 5 ml. 1N sodium methylate solution and then boiled for 10 minutes. Thereafter, the methanol was replaced by ethyl acetate and the ethyl acetate solution washed two or three times with water. After drying and evaporating the solution, the residue was recrystallized twice from 100 ml. methanol/water (1:1), with the addition of active charcoal. There were finally obtained 5.9 g. (56% of theory) N(6)-but-2-enyl-N(6)-(2,5-dimethylbenzyl)-adenosine, which had a melting point of 125°–127°C.

EXAMPLE 5

Preparation of N(6)-(2-Hydroxyethyl)-N(6)-(2-methoxy-5-chlorobenzyl)-adenosine 5.7 g. 6-Chloro-9-($\beta$-D-ribofuranosyl)-purine, 6 g. N-(2-hydroxyethyl)-2-methoxy-5-chlorobenzylamine and 2.5 g. triethylamine were heated under reflux for 2 hours in 100 ml. n-butanol. Subsequently, the solvent was removed in a vacuum and the residue taken up in 100 ml. chloroform. The chloroform phase was washed several times with water, initially with the addition of some dilute hydrochloric acid and thereafter with a dilute solution of sodium bicarbonate. From the so purified chloroform solution, there crystallized out 4.9 g. (53% of theory) N(6)-(2-hydroxyethyl)-N(6)-(2-methoxy-5-chlorobenzyl)-adenosine, which melted at 98°–100°C.

The following compounds were obtained in an analogous manner:
from 6-chloro-9-($\beta$-D-ribofuranosyl)-purine and N-cyclohexylbenzylamine hydrochloride there was obtained N(6)-cyclohexyl-N(6)-benzyl-adenosine, which sintered at about 115°C.; yield 25% of theory;

from 6-chloro-9-(β-D-ribofuranosyl)-purine and N-cycloheptylbenzylamine hydrochloride, there was obtained N(6)-cycloheptyl-N(6)-benzyl-adenosine, which melted at 168°–170°C.; yield 44.5% of theory;

from 6-chloro-9-(β-D-ribofuranosyl)-purine and N-cyclohexyl-2-nitrobenzylamine, there was obtained N(6)-cyclohexyl-N(6)-(2-nitrobenzyl)-adenosine, which melted at 148°–150°C.; yield 30% of theory;

from 6-chloro-9-(β-D-ribofuranosyl)-purine and N-cyclopentyl-2-methylbenzylamine hydrochloride, there was obtained N(6)-cyclopentyl-N(6)-(2-methylbenzyl)-adenosine, which sintered at about 87°C.; yield 25% of theory;

from 6-chloro-9-(β-D-ribofuranosyl)-purine and N-cycloheptyl-2-methylbenzylamine hydrochloride, there was obtained N(6)-cycloheptyl-N(6)-(2-methylbenzyl)-adenosine, which melted at 162°–163°C.; yield 26% of theory;

from triacetyl-6-chloro-9-(β-D-ribofuranosyl)-purine and N-(3-methoxypropyl)-2-methoxybenzylamine, there was obtained N(6)-(3-methoxypropyl)-N(6)-(2-methoxybenzyl)-adenosine, which melted at 123°–125°C.; yield 56% of theory;

from 6-chloro-9-(β-D-ribofuranosyl)-purine and N-cyclohexyl-2,5-dimethylbenzylamine hydrochloride, there was obtained N(6)-cyclohexyl-N(6)-(2,5-dimethylbenzyl)-adenosine, which melted at 170°–172°C.; yield 38% of theory;

from 6-chloro-9-(β-D-ribofuranosyl)-purine and N-cycloheptyl-2,5-dimethylbenzylamine hydrochloride, there was obtained N(6)-cycloheptyl-N(6)-(2,5-dimethylbenzyl)-adenosine, which melted at 168°–170°C.; yield 56% of theory;

from 6-chloro-9-(β-D-ribofuranosyl)-purine and N-cyclopentyl-2-methoxy-5-chlorobenzylamine, there was obtained N(6)-cyclopentyl-N(6)-(2-methoxy-5-chlorobenzyl)-adenosine, which sintered at 78°–80°C.; yield 51% of theory;

from 6-chloro-9-(β-D-ribofuranosyl)-purine and N-allyl-2,5-dimethylbenzylamine, there was obtained N(6)-allyl-N(6)-(2,5-dimethylbenzyl)-adenosine, which sintered at 58°–60°C.; yield 53% of theory;

from 6-chloro-9-(β-D-ribofuranosyl)-purine and N-methallyl-2,5-dimethylbenzylamine, there was obtained N(6)-methallyl-N(6)-(2,5-dimethylbenzyl)-adenosine, which melted at 103°–105°C.; yield 56% of theory;

from 6-chloro-9-(β-D-ribofuranosyl)-purine and N-cyclopentyl-2-methylthio-5-methylbenzylamine, there was obtained N(6)-cyclopentyl-N(6)-(2-methylthio-5-methylbenzyl)-adenosine, which melted at 109°–111°C.; yield 38% of theory.

EXAMPLE 6

Preparation of 2',3',5'-Tri-O-benzoyl-N(6)-cyclopentyl-N(6)-(2,5-dimethylbenzyl)-adenosine 11.2 g. Benzoyl chloride was added dropwise, with stirring and efficient cooling, to a solution of 4.5 g. N(6)-cyclopentyl-N(6)-(2,5-dimethylbenzyl)-adenosine in 25 ml. anhydrous pyridine. The reaction mixture was left to stand overnight at ambient temperature and was then evaporated in a vacuum and the residue mixed with chloroform and water. The chloroform phase was washed several times with water, dried and evaporated. The syrupy, non-crystallizing residue was dissolved in ether, the ethereal solution was treated with active charcoal and the product finally precipitated out by the dropwise addition of the ethereal solution into well cooled ligroin. There were obtained 6.8 g. (89% of theory) chromatographically pure, amorphous 2',3',5'-tri-O-benzoyl-N(6)-cyclopentyl-N(6)-(2,5-dimethylbenzyl)-adenosine, which sintered at about 50°C.

EXAMPLE 7

Preparation of 2',3',5'-Tri-O-acetyl-N(6)-cyclopentyl-N(6)-(2,5-dimethylbenzyl)-adenosine 18 ml. Acetic anhydride were added, with stirring and ice cooling, to a solution of 4.5 g. N(6)-cyclopentyl-N(6)-(2,5-dimethylbenzyl)-adenosine, in 25 ml. anhydrous pyridine. The reaction mixture was left to stand overnight at ambient temperature and then evaporated in a vacuum. The residue was mixed with ether and water and the ethereal phase washed several times with water. The reaction mixture was further worked up in the manner described in Example 6. There were obtained 4.7 g. (81% of theory) chromatographically pure, amorphous 2',3',5'-tri-O-acetyl-N(6)-cyclopentyl-N(6)-(2,5-dimethylbenzyl)-adenosine, which sintered at about 50°C.

The following compounds were obtained in an analogous manner:

from N(6)-isopropyl-N(6)-benzyl-adenosine and acetic anhydride, there was obtained 2',3',5'-tri-O-acetyl-N(6)-isopropyl-N(6)-benzyl-adenosine, which sintered at 55°–59°C.; yield 70% of theory;

from N(6)-cyclohexyl-N(6)-(2-nitrobenzyl)-adenosine and acetic anhydride, there was obtained 2',3',5'-tri-O-acetyl-N(6)-cyclohexyl-N(6)-(2-nitrobenzyl)-adenosine, which sintered at 78°–80°C.; yield 72% of theory;

from N(6)-allyl-N(6)-(2,5-dimethylbenzyl)-adenosine and acetic anhydride, there was obtained 2',3',5'-tri-O-acetyl-N(6)-allyl-N(6)-(2,5-dimethylbenzyl)-adenosine, which sintered at 49°–52°C.; yield 48% of theory;

from N(6)-but-2-enyl-N(6)-(2,5-dimethylbenzyl)-adenosine and acetic anhydride, there was obtained 2',3',5'-tri-O-acetyl-N(6)-but-2-enyl-N(6)-(2,5-dimethylbenzyl)-adenosine, which sintered at 46°–49°C.; yield 88% of theory;

from N(6)-methallyl-N(6)-(2,5-dimethylbenzyl)-adenosine and acetic anhydride, there was obtained 2',3',5'-tri-O-acetyl-N(6)-methallyl-N(6)-(2,5-dimethylbenzyl)-adenosine, which sintered at 53°–55°C.; yield 77% of theory;

from N(6)-2-hydroxyethyl-N(6)-(2-methoxy-5-chlorobenzyl)-adenosine and acetic anhydride, there was obtained 2',3',5'-tri-O-acetyl-N(6)-2-acetoxyethyl-N(6)-(2-methoxy-5-chlorobenzyl)-adenosine, which sintered at 58°–62°C.; yield 86% of theory.

The compounds of this invention are, as indicated above, useful to decrease serum lipids in mammals. The effectiveness of the instant compounds on the lowering of triglycerides in the blood serum was determined following the procedure of Kreutz and Eggstein, modified by Schmidt et al (Z. klin. Chem. u. klin. Biochem., 6, 1968, 156–159). The procedure was carried out using for each compound ten healthy male Sprague-Dawley rats, each weighing about 200 g. The animals were kept without food for 16 to 18 hours before application. The compounds were administered intraperitoneally (i.p.) in an aqueous buffered solution. The control group in each instance received only the solvent in the same manner of application. One hour after application of the compounds (or of the solvent alone for establishing the control values) the animals were killed and exsanguinated and in the obtained serum thereof the triglycerides were determined enzymatically according to the method of Kreutz and Eggstein, modified by Schmidt et al, supra.

The results are set forth in the following Table 1, expressed as percentage reduction of the triglycerides in the serum of treated animals relative to the control animals.

TABLE 1

TRIGLYCERIDE DEPRESSION IN RATS

| Test Compound | Prep. Ex. | Dosage (mg/kg) | Depression of Triglycerides (in %) |
|---|---|---|---|
| N(6)-Cyclohexyl-N(6)-(2-nitrobenzyl)-adenosine | 5 | 0.1 | 26 |
| N(6)-Methallyl-N(6)-(2,5-dimethylbenzyl)-adenosine | 5 | 0.1 | 30 |
| N(6)-Cyclopentyl-N(6)-(2-methylmercapto-5-methyl-benzyl)-adenosine | 5 | 0.1 | 26 |
| N(6)-Cyclopentyl-N(6)-(2,4-dimethylbenzyl)-adenosine | 3 | 0.1 | 32 |
| N(6)-Cyclopentyl-N(6)-(3,4-dimethylbenzyl)-adenosine | 3 | 0.1 | 42 |
| N(6)-Cycloheptyl-N(6)-benzyl-adenosine | 5 | 0.1 | 26 |
| N(6)-Cyclopentyl-N(6)-(2-methylbenzyl)-adenosine | 5 | 0.1 | 32 |
| N(6)-Cyclohexyl-N(6)-(2,5-dimethylbenzyl)-adenosine | 5 | 0.025 | 34 |
|  |  | 0.1 | 46 |
| N(6)-Cycloheptyl-N(6)-(2,5-dimethylbenzyl)-adenosine | 5 | 0.1 | 26 |
| N(6)-Cyclopentyl-N(6)-(2,5-dimethylbenzyl)-adenosine | 3 | 0.025 | 35 |
| Nicotinic Acid (Comparison Compound) |  | 10 | 28 |

The data in Table 1 show a substantially better effectiveness of the new compounds as compared with the comparison standard, nicotinic acid; with the latter, 10 mg/kg i.p. were required to achieve a triglyceride depression of 28%. The instant compounds achieved the same, or better, reduction in triglycerides at much lower dosages, e.g., at 0.1 or even 0.025 mg/kg.

As previously indicated, the adenosine derivatives of this invention are readily adapted to therapeutic use as fat-affecting agents. The toxicity of the compounds of the invention has been found to be quite low or substantially non-existent when they are administered in amounts that are sufficient to achieve the desired therapeutic effect. Moreover, no other pharmacological side effects have been observed to occur as a result of their administration.

In accordance with the compositions and methods of treatment of the present invention, the compounds can be variously formulated or given per se. For instance, the compounds and compositions can be given via the oral route. However, the compounds can also be administered as parenterals in the form of their solutions or suspensions. The compounds can be administered either alone and/or preferably in combination with a pharmaceutically acceptable carrier, and such administration can be carried out in both single and multiple dosages. More particularly, the compounds of this invention can be administered in a wide variety of different dosage forms wherein they are combined with various pharmaceutically acceptable inert carriers in the form of tablets, capsules, dragees, syrups, suspensions, solutions, drops, suppositories, and the like. Such carriers include solid diluents or fillers, liquid aqueous media and various non-toxic organic solvents, etc. For this purpose, the active material is mixed with a solid or liquid pharmaceutical carrier or diluent and the mixture subsequently brought into the desired form. Examples of solid materials include lactose, mannitol, starch, talc, methyl-cellulose, silicic acid, calcium phosphate, magnesium stearate, agar-agar and gelatine to which, if desired, coloring and/or flavoring materials can be added. Liquid carrier materials must be sterile when used for injection solutions and are preferably placed into ampoules.

In general, the therapeutically effective compounds are present in such dosage forms at concentration levels ranging from about 0.01 to about 90% by weight of the total composition, i.e., in amounts which are sufficient to provide the desired unit dosage. In dosage unit form, the compounds as set out herein are used in amounts of from 0.1 to 50 mg active ingredient per dosage unit. Preferably, the compositions are compounded so that for parenteral administration, 0.5–5 mg active compound/dosage unit is present and for oral administration 2–10 mg of compound/dosage unit.

The precise dosages of compound to be administered to a given patient will depend on a number of factors, but generally a dosage in the range of 0.01 to 20 mg/kg per day will result in efficacious effects both by the oral and parenteral route, preferably of 0.5 to 5 mg/kg per day.

It will be understood that the specification and examples are illustrative but not limitative of the present invention and that other embodiments within the spirit and scope of the invention will suggest themselves to those skilled in the art.

What is claimed is:

1. Therapeutic composition having anti-lipolytic, anti-hyperlipaemic and anti-hypercholesterolaemic action comprising a pharmaceutically acceptable carrier and, in effective amounts, an N(6)-disubstituted adenosine compound of the formula:

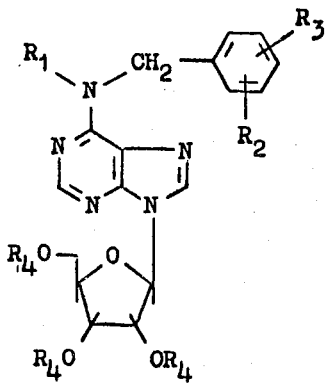

wherein
  $R_1$ is lower alkyl of up to 8 carbon atoms substituted by at least one of hydroxyl, alkoxy or acyloxy of up to 8 carbon atoms each; cycloalkyl of from 3 to 9 carbon atoms; or lower alkenyl of up to 8 carbon atoms;
  $R_2$ and $R_3$ are individually hydrogen, halogen, nitro, lower alkyl, lower alkoxy or lower alkylthio of up to 8 carbon atoms; and
  $R_4$ is hydrogen or acyl of up to 8 carbon atoms;
and the pharmacologically acceptable salts thereof.

2. Method of treating a mammal to decrease serum lipides in said mammal which comprises administering to said mammal an effective amount of an N(6)-disubstituted adenosine compound of the formula

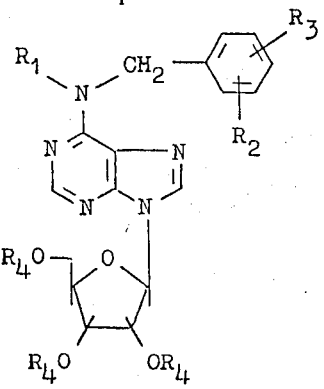

wherein
  $R_1$ is lower alkyl of up to 8 carbon atoms substituted by at least one of hydroxyl, alkoxy or acyloxy of up to 8 carbon atoms each; cycloalkyl of from 3 to 9 carbon atoms; or lower alkenyl of up to 8 carbon atoms;
  $R_2$ and $R_3$ are individually hydrogen, halogen, nitro, lower alkyl, lower alkoxy or lower alkylthio of up to 8 carbon atoms; and
  $R_4$ is hydrogen or acyl of up to 8 carbon atoms;
and the pharmacologically acceptable salts thereof.

3. Method as claimed in claim 2 wherein said compound is applied at a dosage of 0.01 to 20 mg./kg. per day.

4. Method as claimed in claim 2, wherein said compound is at least one of the following: N(6)-cyclohexyl-N(6)-(2-nitrobenzyl)-adenosine; N(6)-methallyl-N(6)-(2,5-dimethylbenzyl)-adenosine; N(6)-cyclopentyl-N(6)-(2-methylmercapto-5-methyl-benzyl)-adenosine; N(6)-cyclopentyl-N(6)-(2,4-dimethylbenzyl)-adenosine; N(6)-Cyclopentyl-N(6)-(3,4-dimethylbenzyl)-adenosine; N(6)-cycloheptyl-N(6)-benzyladenosine; N(6)-cyclopentyl-N(6)-(2-methylbenzyl)-adenosine; N(6)-cyclohexyl-N(6)-(2,5-dimethylbenzyl)-adenosine; N(6)-cycloheptyl-N(6)-(2,5-dimethylbenzyl)-adenosine; and N(6)-cyclopentyl-N(6)-(2,5-dimethylbenzyl)-adenosine.

5. Method as claimed in claim 2 wherein $R_1$ in the formula is hydroxyalkyl of up to 8 carbon atoms.

6. Method as claimed in claim 2 wherein $R_1$ is alkoxyalkyl of up to 16 carbon atoms.

7. Method as claimed in claim 2 wherein $R_1$ is alkanoyloxyalkyl wherein each alkyl moiety is up to 8 carbon atoms.

8. Method as claimed in claim 2 wherein $R_1$ is cycloalkyl of 5 to 7 ring carbon atoms.

9. Method as claimed in claim 2 wherein $R_1$ is lower alkenyl of up to 8 carbon atoms.

10. Method as claimed in claim 2 wherein $R_2$ is hydrogen.

11. Method as claimed in claim 2 wherein $R_2$ is halogen.

12. Method as claimed in claim 2 wherein $R_2$ is nitro.

13. Method as claimed in claim 2 wherein $R_2$ is alkyl of 1 to 8 carbon atoms.

14. Method as claimed in claim 2 wherein $R_2$ is alkoxy of 1 to 8 carbon atoms.

15. Method as claimed in claim 2 wherein $R_2$ is alkylthio of 1 to 8 carbon atoms.

16. Method as claimed in claim 2 wherein $R_3$ is hydrogen.

17. Method as claimed in claim 2 wherein $R_3$ is halogen.

18. Method as claimed in claim 2 wherein $R_3$ is nitro.

19. Method as claimed in claim 2 wherein $R_3$ is alkyl of 1 to 8 carbon atoms.

20. Method as claimed in claim 2 wherein $R_3$ is alkoxy of 1 to 8 carbon atoms.

21. Method as claimed in claim 2 wherein $R_3$ is alkylthio of 1 to 8 carbon atoms.

22. Method as claimed in claim 2 wherein $R_4$ is hydrogen.

23. Method as claimed in claim 2 wherein $R_4$ is alkanoyl of up to 8 carbon atoms.

24. Method as claimed in claim 2 wherein $R_4$ is hydrogen and $R_1$ is substituted alkyl of 1 to 8 carbon atoms.

25. Method as claimed in claim 2 wherein said compound is designated N(6)-cyclopentyl-N(6)-(2,5-dimethylbenzyl)-adenosine.

26. Method as claimed in claim 2 wherein said compound is designated N(6)-cyclopentyl-N(6)-(2,4-dimethylbenzyl)-adenosine.

27. Method as claimed in claim 2 wherein said compound is designated N(6)-cyclopentyl-N(6)-(3,4-dimethylbenzyl)-adenosine.

28. Method as claimed in claim 2 wherein said compound is designated N(6)-cyclopentyl-N(6)-(2-methylbenzyl)-adenosine.

29. Method as claimed in claim 2 wherein said compound is designated N(6)-cyclohexyl-N(6)-(2,5-dimethylbenzyl)-adenosine.

* * * * *